United States Patent
Dobrilovic

(10) Patent No.: US 10,182,913 B2
(45) Date of Patent: Jan. 22, 2019

(54) HEART VALVE SIZING RING FOR VALVE-SPARING AORTIC ROOT REMODELING PROCEDURES

(71) Applicant: Nikola Dobrilovic, Providence, RI (US)

(72) Inventor: Nikola Dobrilovic, Providence, RI (US)

(*) Notice: Subject to any disclaimer, the term of this patent is extended or adjusted under 35 U.S.C. 154(b) by 692 days.

(21) Appl. No.: 14/051,787

(22) Filed: Oct. 11, 2013

(65) Prior Publication Data

US 2014/0107774 A1   Apr. 17, 2014

Related U.S. Application Data

(63) Continuation-in-part of application No. 13/658,050, filed on Oct. 23, 2012, and a continuation-in-part of application No. 13/871,327, filed on Apr. 26, 2013.

(60) Provisional application No. 61/713,115, filed on Oct. 12, 2012.

(51) Int. Cl.
*A61F 2/24* (2006.01)
*A61B 17/04* (2006.01)
*A61B 17/02* (2006.01)
*A61B 17/00* (2006.01)

(52) U.S. Cl.
CPC ........ *A61F 2/2496* (2013.01); *A61B 17/0483* (2013.01); *A61B 17/0293* (2013.01); *A61B 2017/00725* (2013.01); *A61B 2017/00783* (2013.01)

(58) Field of Classification Search
CPC ....................................................... A61F 2/24
USPC ....................................................... 623/2.11
See application file for complete search history.

(56) References Cited

U.S. PATENT DOCUMENTS

| | | |
|---|---|---|
| 5,071,431 A | 12/1991 | Sauter et al. |
| 5,360,014 A | 11/1994 | Sauter et al. |
| 5,489,296 A | 2/1996 | Love et al. |
| 5,814,096 A | 9/1998 | Lam et al. |
| 5,843,177 A | 12/1998 | Vanney et al. |
| 6,019,739 A | 2/2000 | Rhee et al. |
| 6,110,200 A | 8/2000 | Hinnenkamp |
| 6,458,155 B1 | 10/2002 | Van Nguyen et al. |
| 6,678,962 B1 | 1/2004 | Love et al. |
| 6,702,763 B2 | 3/2004 | Murphy et al. |
| 6,719,785 B2 | 4/2004 | Schoon et al. |

(Continued)

FOREIGN PATENT DOCUMENTS

JP   11206739 A   8/1999

OTHER PUBLICATIONS

Peters Surgical, "uniRing Universal Annuloplasty System", 2007 http://www.zenomedical.com/Images/Products/Brochures/uniRing.pdf.

*Primary Examiner* — Matthew Schall
(74) *Attorney, Agent, or Firm* — McInnes & McLane, LLP

(57) ABSTRACT

A heart valve sizing ring is disclosed. The sizing ring includes an outer ring and an inner ring configured and arranged to couple to the outer ring. A tubular portion extends from the inner ring and has a plurality of suture holders arranged about an upper end thereof. The outer ring and inner ring having a pair of complementary mating surfaces configured and arranged to grip sutures therebetween when coupled together. When coupled around sutures, the assembled ring may be tightened down against the heart valve to test the fit as if the sizing ring were a similarly sized prosthetic heart valve ring. Commissures of the heart valve may be suspended from the suture holders of the tubular portion. The surgeon can then remove the sizing ring and replace it with a prosthetic ring.

8 Claims, 2 Drawing Sheets

(56) References Cited

U.S. PATENT DOCUMENTS

| | | |
|---|---|---|
| 7,338,484 B2 | 3/2008 | Schoon et al. |
| 2008/0033544 A1 | 2/2008 | Lemmon |
| 2009/0210051 A1 | 8/2009 | Camedda et al. |
| 2010/0262043 A1 | 10/2010 | Sauter et al. |
| 2012/0065729 A1* | 3/2012 | Pintor et al. ................ 623/2.11 |
| 2012/0071968 A1 | 3/2012 | Li et al. |

* cited by examiner

HEART VALVE SIZING RING FOR VALVE-SPARING AORTIC ROOT REMODELING PROCEDURES

CROSS-REFERENCE TO RELATED APPLICATION

This patent document claims priority to earlier filed U.S. Provisional Patent Application Ser. No. 61/713,115, filed Oct. 12, 2012, and is a continuation-in-part of U.S. patent application Ser. No. 13/658,050, filed Oct. 23, 2012, and U.S. patent application Ser. No. 13/871,327, filed on Apr. 26, 2013, the entire contents of which are incorporated herein by reference.

BACKGROUND OF THE INVENTION

1. Technical Field

The present patent document relates generally to heart valve sizing rings and more particularly to a heart valve sizing ring configured for valve-sparing aortic root remodeling procedures.

2. Background of the Related Art

Referring to FIGS. 1 and 2, during valve-sparing aortic root remodeling procedures sutures 14 are aligned at the base of the heart valve 10. The aortic wall is resected and sculpted to preserve three anchor points for the heart valve where the leaflets 12 meet, i.e. the commissures 16. Sutures 18 are placed above the commissures 16. The sutures 14 at the base of the valve 10 are used to anchor the graft to the heart and to stabilize (and often "downsize") the aortic root. The sutures 18 above the commissures 16 are anchored to the upper "tube" portion of the graft where they are positioned high enough to allow the commissures 16 to be "resuspended" helping to correct geometry of the valve 10.

However, if the correct graft size is not selected during the repair, the surgeon may not be able to properly reshape the valve 10, thereby leading prolonged and/or suboptimal surgical operations which could lead to complications and poor outcomes.

Therefore, there is a perceived need in the industry for a method and device to allow a surgeon to easily size and test a valve repair in valve-sparing aortic root remodeling procedures.

SUMMARY OF THE INVENTION

The present invention solves the problems of the prior art by providing a heart valve sizing ring system that includes and outer ring and an interlocking inner ring. The inner ring further includes a tubular portion that can be used to test and simulate whether the heart valve has been properly sized prior to installing a permanent graft prosthesis. The tubular portion may additionally include suture holders at the top to aid the surgeon in recreating valve geometry and function by "suspending" the commissures within the tubular portion thus assisting with evaluation/testing of proper graft/valve size selection.

BRIEF DESCRIPTION OF THE DRAWINGS

These and other features, aspects, and advantages of the present invention will become better understood with reference to the following description, appended claims, and accompanying drawings where:

DESCRIPTION OF THE PREFERRED EMBODIMENT

Figure 1:
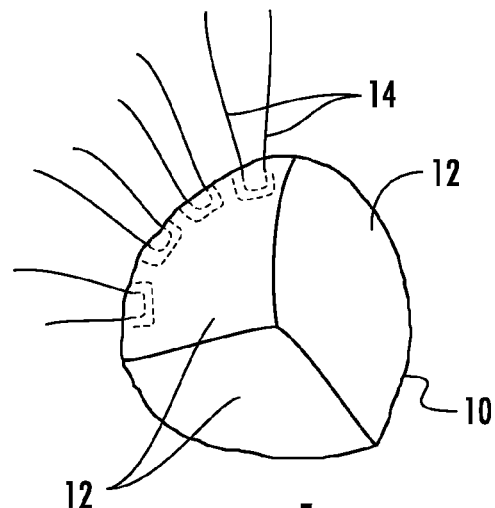
FIG. 1 shows an aortic heart valve with sutures being installed at the base of the valve.
Figure 2:
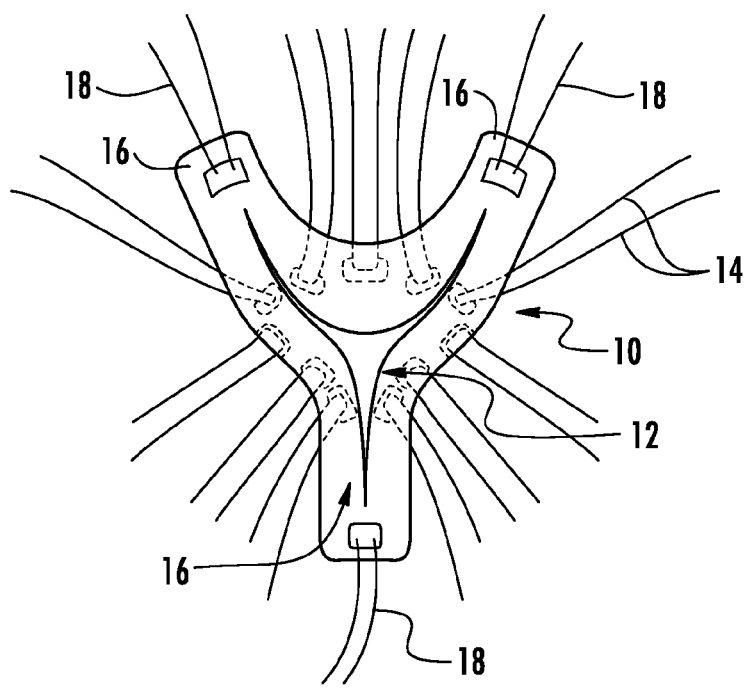
FIG. 2 shows an aortic heart valve after excess and/or diseased aortic tissue has been resected using a technique that preserves the valve itself More sutures are placed circumferentially.
Figure 3:
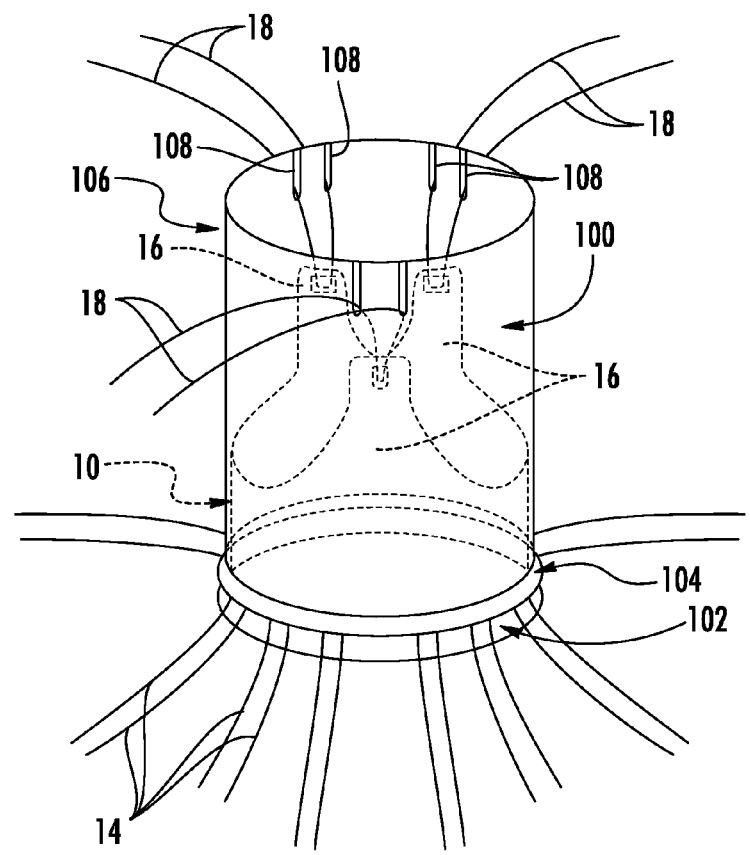
FIG. 3 shows the heart valve sizing system supporting the heart valve therein for testing the size of the graft prior to placement.
Figure 4:
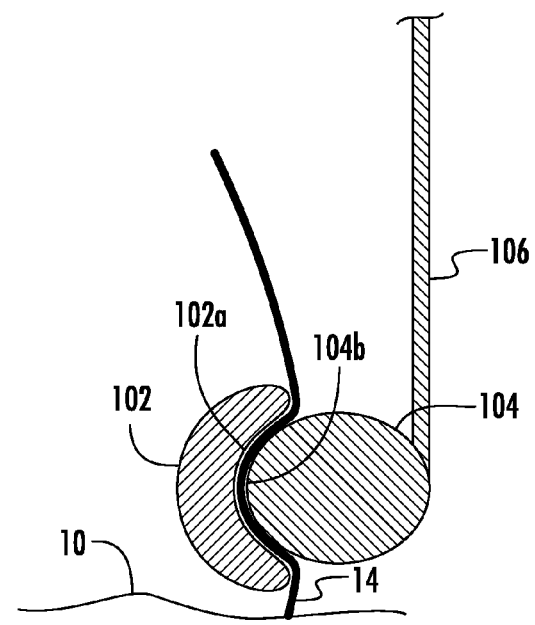
FIG. 4 shows a partial cross-section of a suture being trapped between the inner ring and the outer ring.

Referring now to FIGS. 3 and 4, a first embodiment of the heart valve sizing ring is shown generally over a heart valve that has been resected and sculpted at 100. The heart valve sizing ring 100 includes an outer ring 102, and inner ring 104 that interlocks with the outer ring 102, and a tubular portion 106 (simulating a graft) extending from the inner ring 104.

Sutures 14 at the base of the heart valve 10 are captured between the inner and outer rings 102,104, thereby temporarily anchoring the heart valve sizing ring 100 to the heart valve 10. The inner and outer rings 102, 104, may include a concave and convex surfaces 102a, 104b, to facilitate retention of the sutures 14. The surfaces may optionally be coated with a rubber-type of coating to gently grip the sutures and prevent slipping. Because the inner and outer rings 102, 104 form a rigid structure, the precise size of the annular diameter is provided during evaluation.

The valve commissures 16 are suspended temporarily using the suture holders 108, such as slots, via the commissure sutures 18. This allows for the valve leaflet 12 distance and apposition to be properly evaluated by creating a "quick preview" of what valve function would be like should a graft of that size be selected. Several different graft sizes can be tested and compared in a relatively short time prior to final graft selection. Note that this system can be used with either a "straight" tube graft or with a "Valsalva" type of tube graft (in which the sides of the graft "bow" outward slightly).

The pictured slots as suture holders 108 represent one embodiment that may facilitate commissural suspension, though, this could be accomplished by other mechanisms as well, such as clipping the commissure sutures 18 to the tube wall, etc. The material of the tubular portion 106 is not restricted and can be made of a stiffer material than the graft prosthesis if it is only being used for sizing purposes. The slots 108 can have an additional rubber-type of coating or some other material that is advantages in gently gripping and holding the commissure sutures 18.

It would be appreciated by those skilled in the art that various changes and modifications can be made to the illustrated embodiments without departing from the spirit of the present invention. All such modifications and changes are intended to be within the scope of the present invention

I claim:

1. A heart valve sizing ring, comprising:
an outer ring;
an inner ring configured and arranged to removably couple to the outer ring;
the outer ring and inner ring having a pair of complementary mating surfaces configured and arranged to grip annular sutures around the base of a heart valve therebetween when coupled together, the sutures being slidably adjustable between the inner ring and outer ring when gripped therebetween;
a tubular portion extending from the inner ring and away from the outer ring when coupled together, the tubular portion having an upper end with an opening distal to the inner ring and coupled outer ring; and a plurality of suture holders spaced about the upper end of the tubular portion, said suture holders configured and arranged to grip commissure sutures to suspend a heart valve leaflets within the tubular portion.

2. The heart valve sizing ring of claim 1, wherein the outer ring further comprises a defect forming a break in the outer ring.

3. The heart valve sizing ring of claim 1, wherein the outer ring has a concave surface on an inner portion thereof and the inner ring has a convex surface on an outer portion thereof that snap-fit together.

4. The heart valve sizing ring of claim 1, wherein the suture holders are slots.

5. The heart valve sizing ring of claim 4, wherein the slots have a coating to aid in gently gripping sutures.

6. The heart valve sizing ring of claim 1, wherein the suture holders are clips.

7. The heart valve sizing ring of claim 1, wherein the tubular portion is straight.

8. The heart valve sizing ring of claim 1, wherein the tubular portion is a Valsalva-type tubular graft.

\* \* \* \* \*